(12) United States Patent
Siegel

(10) Patent No.: US 8,839,657 B2
(45) Date of Patent: Sep. 23, 2014

(54) CALIBRATION SYSTEM AND METHOD FOR ACOUSTIC PROBES

(75) Inventor: Jonathan H. Siegel, Skokie, IL (US)

(73) Assignee: Northwestern University, Evanston, IL (US)

( * ) Notice: Subject to any disclaimer, the term of this patent is extended or adjusted under 35 U.S.C. 154(b) by 256 days.

(21) Appl. No.: 13/471,941

(22) Filed: May 15, 2012

(65) Prior Publication Data

US 2012/0291520 A1 Nov. 22, 2012

Related U.S. Application Data

(60) Provisional application No. 61/487,796, filed on May 19, 2011.

(51) Int. Cl.
*G01N 29/30* (2006.01)

(52) U.S. Cl.
CPC ...................................... *G01N 29/30* (2013.01)
USPC .......................................................... 73/1.82

(58) Field of Classification Search
USPC .............. 73/1.82, 702, 703, 865.6, 597, 598, 73/585; 367/13
See application file for complete search history.

(56) References Cited

U.S. PATENT DOCUMENTS

| | | | |
|---|---|---|---|
| 4,936,143 A * | 6/1990 | Schutten et al. | ................. 73/597 |
| 5,594,174 A | 1/1997 | Keefe | |
| 5,651,371 A | 7/1997 | Keefe | |
| 6,139,507 A | 10/2000 | Jeng | |
| 7,715,577 B2 | 5/2010 | Allen et al. | |
| 2005/0217346 A1* | 10/2005 | Nagarkatti et al. | ............ 73/1.16 |
| 2007/0219458 A1 | 9/2007 | Jeng | |
| 2008/0228101 A1 | 9/2008 | Allen et al. | |

* cited by examiner

*Primary Examiner* — Daniel S Larkin
*Assistant Examiner* — Irving A Campbell
(74) *Attorney, Agent, or Firm* — Klintworth & Rozenblat IP LLC

(57) ABSTRACT

An acoustic probe calibration system includes a waveguide and a moveable piston. The waveguide extends from a front end to an opposite back end along a longitudinal axis and defines a cavity extending from the front end to the back end. The piston is disposed within the cavity of the waveguide and is configured to move within the cavity of the waveguide along the longitudinal axis of the waveguide. An acoustic probe is inserted into the waveguide to define an interior chamber between the acoustic probe and the piston. The acoustic probe determines pressure responses to acoustic stimuli inside the interior chamber. The piston is moveable to a plurality of different positions within the waveguide to change a size of the interior chamber such that the acoustic probe can determine the pressure responses within the varying-size interior chamber.

16 Claims, 3 Drawing Sheets

CALIBRATION SYSTEM AND METHOD FOR ACOUSTIC PROBES

CROSS-REFERENCE TO RELATED APPLICATIONS

This application claims priority benefit to U.S. Provisional Application No. 61/487,796, which was filed on 19 May 2011 (the "'796 application"). The entire subject matter of the '796 application is incorporated by reference.

STATEMENT REGARDING FEDERALLY SPONSORED RESEARCH OR DEVELOPMENT

This invention was made with government support under grant number R01 DC008420 awarded by the National Institutes of Health (National Institute on Deafness and Other Communication Disorders). The government has certain rights in the invention.

BACKGROUND

Acoustic probes can include a first transducer that generates oscillatory flow, such as sound waves, within a volume and a second transducer that measures an acoustic pressure within the volume. Among other things, the acoustic probes can be used to measure acoustic pressures within the human ear canal. Recent movement in the field of hearing research and testing has included work in calibrating acoustic stimuli in units of the component of the sound pressure that travels toward an eardrum, or forward pressure, thus minimizing the impact of standing waves created by interaction between the forward pressure and the component reflected from the eardrum. Such calibration can be superior in controlling stimulus levels to an ear than some other known methods.

In order to calibrate an acoustic probe, the Thévenin source pressure and impedance of the acoustic probe can be determined using a series of cylindrical cavities or waveguides of different lengths. For example, a series of rigid tubes of different, or stepped, lengths may be used. The brass tubes can be fixed to a rigid base plate and the acoustic probe manually inserted into each of the tubes in succession. When inserted into a tube, the first transducer of the acoustic probe emits acoustic stimuli (e.g., a series of pure tones covering a frequency range of interest, MLS sequences, pseudorandom noise, chirps, clicks, and the like) and the second transducer measures the pressure response inside the tube to the acoustic stimuli.

The pressure responses are measured for several or all of the tubes and can be used to solve for the Thévenin source parameters, its source pressure and impedance. The Thévenin source parameters can then be used to calibrate measurements obtained by the acoustic probe in human ear canals. The Thévenin calibration of acoustic probes can be used to improve the accuracy of a variety of hearing measurements in research laboratories, hearing clinics, industrial hearing conservation programs, infant screening programs, school children screening programs, and the like.

However, the known manually intensive calibration procedures of acoustic probes can require significant human interaction and work with both the acoustic probes and the waveguides used to measure the pressure responses. As the amount of manual work involved in calibrating an acoustic probe increases, the amount of time required to calibrate the probe and the possibility of error can increase.

BRIEF DESCRIPTION

In one embodiment, an acoustic probe calibration system is provided. The system includes a waveguide and a moveable piston. The waveguide extends from a front end to an opposite back end along a longitudinal axis and defines a cavity extending from the front end to the back end. The piston is disposed within the cavity of the waveguide and is configured to move within the cavity of the waveguide along the longitudinal axis of the waveguide. An acoustic probe is inserted into the waveguide to define an interior chamber between the acoustic probe and the piston. The acoustic probe measures data that is representative of pressure responses to acoustic stimuli delivered by the probe inside the interior chamber. The piston is moveable to a plurality of different positions within the waveguide to change a size of the interior chamber such that the acoustic probe can measure the data representative of the pressure responses within the varying-size interior chamber.

In another embodiment, a method for calibrating an acoustic probe is provided. The method includes positioning a piston at a first position within a waveguide that extends from a front end to an opposite back end along a longitudinal axis. The waveguide defines a cavity that extends from the front end to the back end. The method also includes inserting the acoustic probe within the waveguide, with the acoustic probe and the piston defining an interior chamber within the cavity of the waveguide that extends from the acoustic probe to the piston. The method further includes emitting acoustic stimuli into the interior chamber from the probe and determining one or more first pressure responses to the acoustic stimuli and moving the piston to a different, second position within the waveguide such that a size of the interior chamber in the waveguide changes. The method also includes emitting acoustic stimuli into the interior chamber from the probe and measuring one or more second pressure responses to the acoustic stimuli.

In another aspect, the method also includes calibrating the acoustic probe based on at least the first and second pressure responses obtained from the differently sized interior chamber of the same waveguide. A greater number of pressure responses may be measured using the varying-size chamber of the same waveguide, such as three, four, five, or more measurements.

In another aspect, moving the piston includes displacing the piston within the waveguide relative to the waveguide without removing the acoustic probe from the waveguide or moving the acoustic probe relative to the waveguide.

BRIEF DESCRIPTION OF THE DRAWINGS

The subject matter described herein will be better understood from reading the following description of non-limiting embodiments, with reference to the attached drawings, wherein below.

DETAILED DESCRIPTION

One or more embodiments described herein provide acoustic probe calibration systems and associated methods that can allow for more convenient automation of a calibration process of an acoustic probe. As described below, a moveable piston in a single waveguide can be moved to several positions within the waveguide to form a varying-size interior chamber. This varying-size interior chamber may be used to determine pressure responses of the waveguide to acoustic stimuli. The piston can be automatically or manually moved to the various positions in an easier and more reliable manner when compared to the use of several different waveguides to determine such pressure responses.

Additionally acoustic leakage of acoustic stimuli from the varying-size interior chamber of the waveguide can be reduced or at least controlled. The resistance of such acoustic leaks increases with a distance of insertion of the piston into the waveguide. Increasing the resistance of the leak can reduce the acoustic leakage to effectively solve the problem of acoustic leakage on calibration of the acoustic probe.

Figure 1:
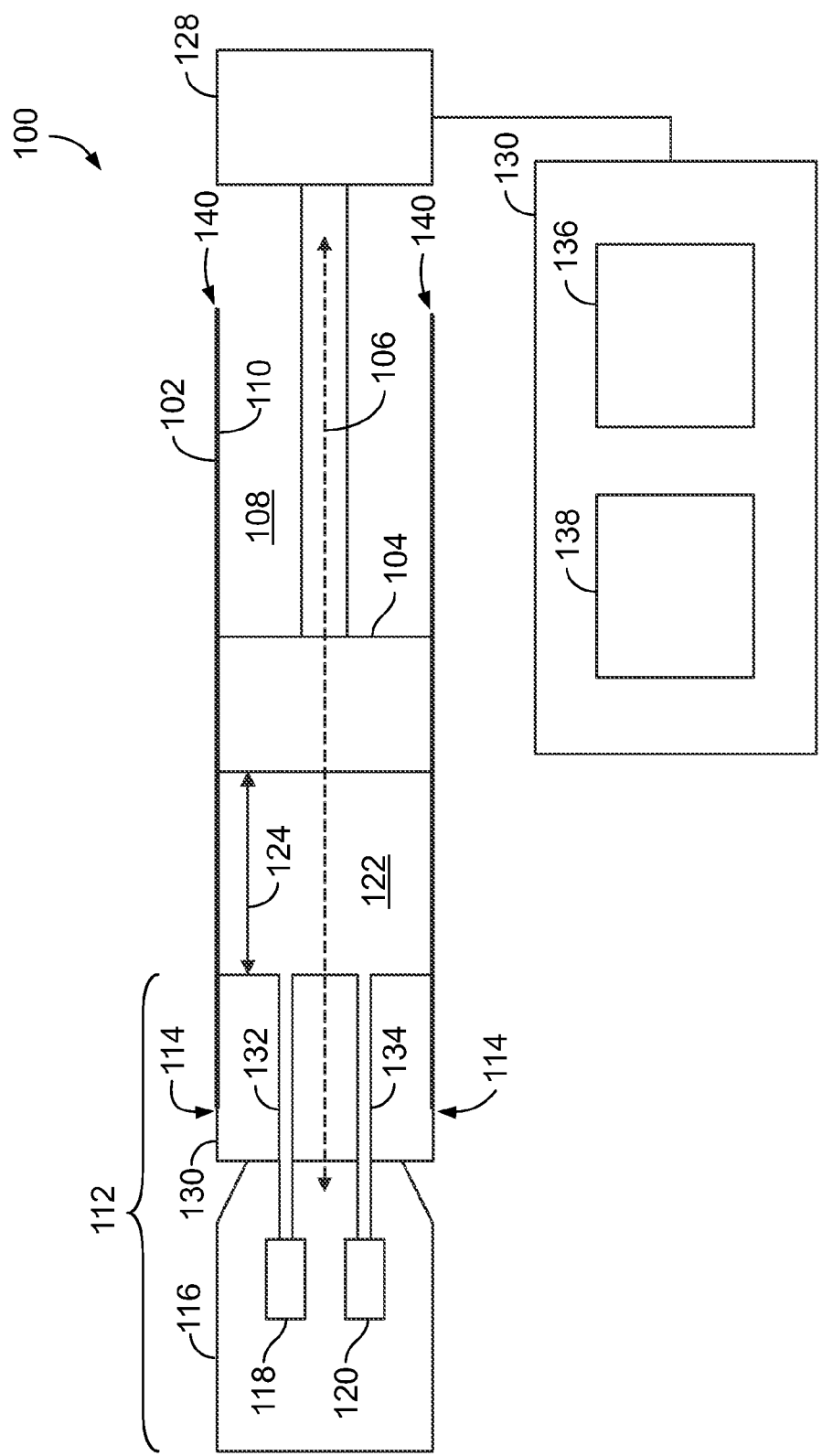
FIG. 1 is a schematic diagram of one embodiment of an acoustic probe calibration system.
Figure 2:
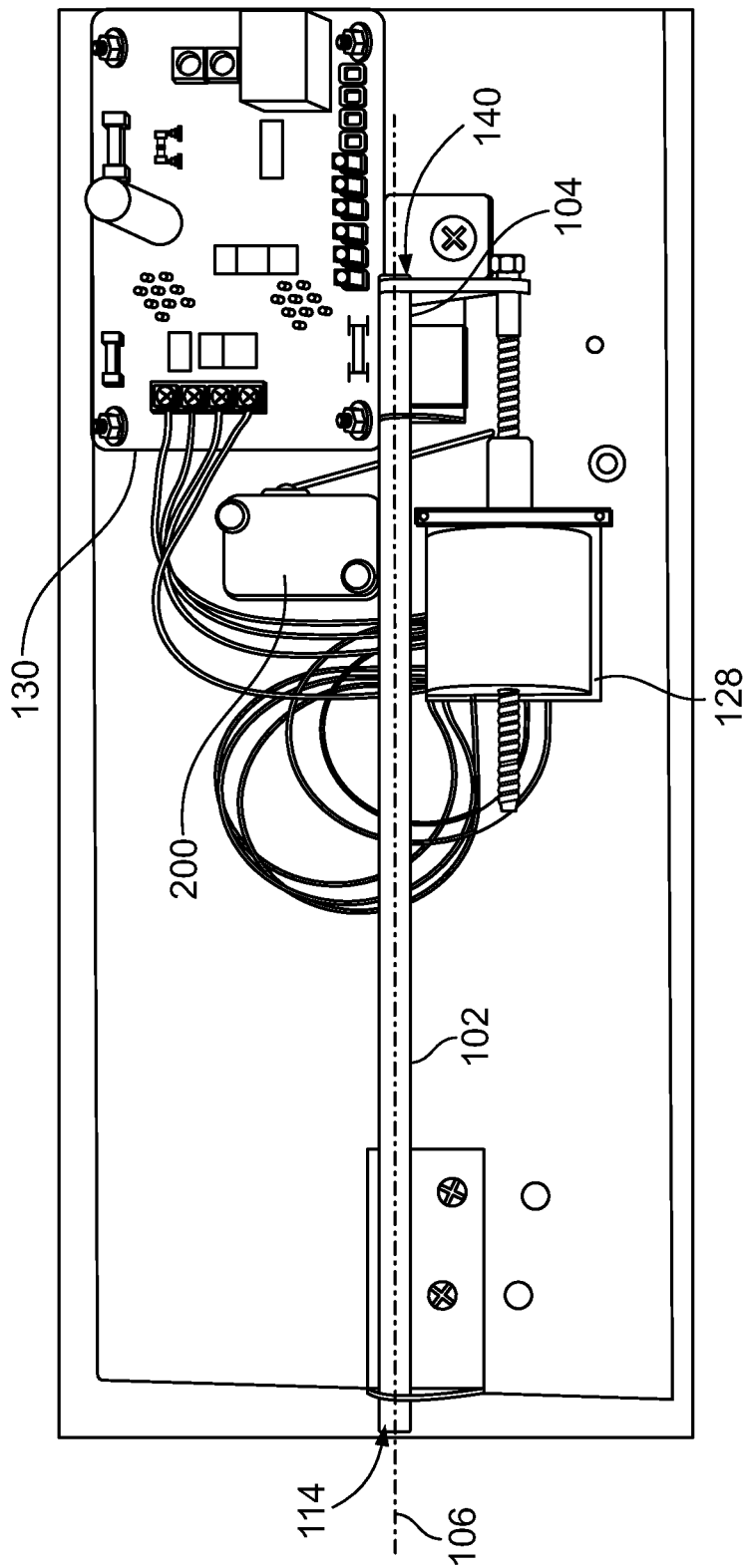
FIG. 2 is a perspective view of the acoustic probe calibration system.

FIG. 1 is a schematic diagram of one embodiment of an acoustic probe calibration system 100. FIG. 2 is a perspective view of the acoustic probe calibration system 100. The system 100 includes a waveguide 102 (also referred to as a "Fixed Cylinder" in FIG. 2) having a moveable piston 104 disposed therein. The waveguide 102 may be a tube or have a tubular shape that is elongated along a longitudinal axis 106. Alternatively, the waveguide 102 may have a different shape. The waveguide 102 can be a one-dimensional waveguide. The waveguide 102 defines a cavity 108 (shown in FIG. 1) that extends along the longitudinal axis 106. The piston 104 is located within the cavity 108 and is moveable relative to the waveguide 102 along the longitudinal axis 106. For example, the piston 104 may move in opposite directions along the longitudinal axis 106 within the waveguide 102. The piston 104 may directly engage an inner surface 110 (shown in FIG. 1) of the waveguide 102 such that the piston 104 seals one end of the waveguide 102. Alternatively, a seal body (e.g., a fluid such as a lubricant, an o-ring, and the like) may be disposed between the piston 104 and the inner surface 110 to seal one end of the waveguide 102. The piston 104 seals the waveguide 102 such that there is relatively low pressure leakage through an interface between the piston 104 and the waveguide 102.

As shown in FIG. 1, an acoustic probe 112 is loaded into a front end 114 (also referred to as "Open End for Probe" in FIG. 2) of the waveguide 102. The acoustic probe 112 includes a body 116 (shown in FIG. 1) with a sound source transducer 118 (shown in FIG. 1) and a microphone 120 (shown in FIG. 1) extending into and/or through the body 116. The probe 112 also includes an ear-tip body 130 that seals the probe 112 to the waveguide 102. The body 130 engages the inner surface 110 (shown in FIG. 1) of the waveguide 102 to seal the other end of the waveguide 102. Alternatively, a seal body may be positioned between the body 130 and the inner surface 110 to create a seal therebetween. In the illustrated embodiment, the body 130, the piston 104, and the waveguide 102 define the boundaries of an interior chamber 122 (shown in FIG. 1) of the waveguide 102. The interior chamber 122 can be a subset or portion of the cavity 108 (shown in FIG. 1) of the waveguide 102. The transducer 118 and the microphone 120 are coupled with coupling tubes 132, 134 that acoustically couple the transducer 118 and the microphone 120 with the interior chamber 122. For example, the coupling tube 132 can transmit the acoustic stimuli emitted by the transducer 118 into the interior chamber 122 and the coupling tube 134 can transmit the response to the acoustic stimuli in the interior chamber 122 to the microphone 120. The sound source transducer 118 can emit acoustic stimuli, such as chirp stimuli, into the interior chamber 122 and the microphone 120 can measure data that is representative of the pressure response to the acoustic stimuli in the interior chamber 122 of the waveguide 102. For example, the microphone 120 can be used to measure an acoustic reflectance of the interior chamber 122 that is based on the pressure response to the acoustic stimuli (e.g., the incident pressure caused by the acoustic stimuli) and the frequency of the acoustic stimuli.

The piston 104 may be a cylindrical body that moves within the waveguide 102 to change a length and/or size of the interior chamber 122. Alternatively, the piston 104 may have a different shape, such as a shape that compliments the interior size of the waveguide 102. The piston 104 may move toward the front end 114 of the waveguide 102 to reduce a length dimension 124 (shown in FIG. 1) of the interior chamber 122. The length dimension 124 extends from the probe 112 (shown in FIG. 1) to the piston 104 in a direction along or parallel to the longitudinal axis 106. As the length dimension 124 increases, the size or volume of the interior chamber 122 increases. Conversely, the piston 104 may retreat from the front end 114 toward an opposite back end 140 of the waveguide 102 to increase the length dimension 124 and the size of the interior chamber 122.

The piston 104 is coupled to an actuator 128 (also referred to as a "Stepper Motor" in FIG. 2) that moves the piston 104 along the longitudinal axis 106 of the waveguide 102 within the cavity 108 (shown in FIG. 1) of the waveguide 102. The actuator 128 can be a linear stepper motor. Alternatively, another type of motor or other type of actuator is used to move the piston 104 within the cavity 108. The actuator 128 is operatively coupled with a controller device 130 (referred to as "Stepper Motor Controller" in FIG. 2). For example, the actuator 128 may be conductively coupled with the controller device 130 separated from the controller device 130 but communicatively coupled with the controller device 130 by a wireless communication link. The controller device 130 drives the actuator 128 to move the piston 104 within the cavity 108 of the waveguide 102. The controller device 130 can include one or more computing devices, such as a computer, one or more computer processors, controllers, hard-wired devices, or one or more other logic-based devices. In the illustrated embodiment, the controller device 130 includes a processor 136 (shown in FIG. 1) that operates based on one or more sets of instructions (e.g., software) stored on a tangible and non-transitory computer readable storage medium, such as a computer memory 138 (shown in FIG. 1). The memory 138 may include one or more computer hard drives, flash drives, RAM, ROM, DVDs, CDs, or other memory devices.

The processor 136 (shown in FIG. 1) operates based on the software stored on the memory 138 (shown in FIG. 1) to move the piston 104 between various positions within the waveguide 102 to correspondingly change the length dimension 124 and size of the interior cavity 122. The controller device 130 may receive input from one or more operator input devices, such as an electronic mouse, stylus, keyboard, touch-screen, microphone, and the like, that are coupled with the controller device 130 by one or more wired and/or wireless communication links. In one embodiment, the actuator 128 can report the position of the piston 104 in the waveguide 102 to the controller device 130 and the controller device 130 may autonomously control the location of the piston 104. For example, the actuator 128 and the controller device 130 may operate in a feedback based loop where the actuator 128 reports the position of the piston 104 to the controller device 130, the controller device 130 determines if the position is at a designated (e.g., desired or input) position, and the controller device 130 then modifies the position of the piston 104, if necessary. Alternatively, the controller device 130 may be coupled with a position sensor that identifies the position of the piston 104 in the waveguide 102.

The controller device 130 may be used to manually and/or automatically control positions of the piston 104 in the waveguide 102. The controller device 130 may receive input instructions from an operator that directs the controller device 130 to move the piston 104 to an operator-selected position in the waveguide 102. The controller device 130 can then communicate a control signal to the actuator 128 to cause the actuator 128 to move the piston 104 to the selected position. Additionally or alternatively, the controller device 130 may autonomously direct the actuator 128 to move the piston 104 to one or more positions, such as a series of predefined positions, for a series of measurements, as described below. The controller device 130 may thus allow for easier and/or more accurate positioning of the piston 104 when compared to manual manipulation of the piston 104.

In operation, the position of the piston 104 within the waveguide 102 can be controlled by the actuator 128 having an interface (e.g., USB interface) with the controller device 130 that allows software control of the position of the piston 104 within the waveguide 102. A mechanical switch 200 (referred to as "Home Position Limit Switch" in FIG. 2) senses a "home" position of the piston 104 at or near the front end 114 of the waveguide 102. In the home position, the length dimension 124 (shown in FIG. 1) between the acoustic probe 112 (shown in FIG. 1) and the piston 104 is relatively small. The length dimension 124 when the piston 104 is at the home position may be set such that a frequency of a first-order half-wave resonance of the cavity in response to the chirp stimuli or other acoustic output of the acoustic probe 112 is increased relative to other frequencies.

The controller device 130 directs the actuator 128 to withdraw the piston 104 toward the back end 140 of the waveguide 102 and to increase the length dimension 124 (shown in FIG. 1) and the size of the interior chamber 122 (shown in FIG. 1) relative to the home position of the piston 104. As the size of the interior chamber 122 increases, a resonant frequency of the cavity in response to the chirp stimuli or other acoustic stimuli of the acoustic probe 112 decreases. The controller device 130 may move the piston 104 to various positions within the waveguide 102 and the acoustic probe 112 may measure frequency responses of the waveguide 102 at the various sizes of the interior chamber 122 that correspond with the positions of the piston 104. Movements of the piston 104 may be in units of resolution of the actuator 128 relative to the home position of the piston 104. In one embodiment, a calibration curve for the acoustic probe 112 may be constructed by measuring the frequency of half wave resonance as a function of position of the piston 104 in the waveguide 102. Successful Thévenin calibration of the acoustic probe 112 may depend on measuring frequency responses with the acoustic probe 112 for a predetermined set of length dimensions 124 and/or sizes of the interior cavity 122. In another embodiment, a human operator may control the locations of the piston 104 by manually moving the piston 104 within the waveguide 102.

Using the software controlled actuator 128 to control the position of the piston 104 within the waveguide 102 can provide an automated procedure for calibrating the acoustic probe 112. The controller device 130 can control the position of the piston 104 in a single waveguide 102 such that Thévenin calibration of the acoustic probe 112 is more accurate and reliable than manual insertion of the acoustic probe 112 into multiple, different tubes of different lengths. The position of the piston 104 can be more accurately controlled in repeated calibrations. The use of a single waveguide 102 as opposed to several tubes can reduce additional sources of error in the Thévenin calibration.

In one embodiment, the Thévenin calibration of the acoustic probe 112 can be automated such that an operator of the system 100 initiates the calibration and the controller device 130 controls the positions of the piston 104 at which the acoustic probe 112 transmits stimuli and measures data that is representative of pressure responses to the acoustic stimuli. The controller device 130 may control when the acoustic probe 112 transmits the stimuli and measures the data that is representative of the pressure responses and, based thereon, generate calibration curves and/or otherwise calibrate the acoustic probe 112.

Figure 3:
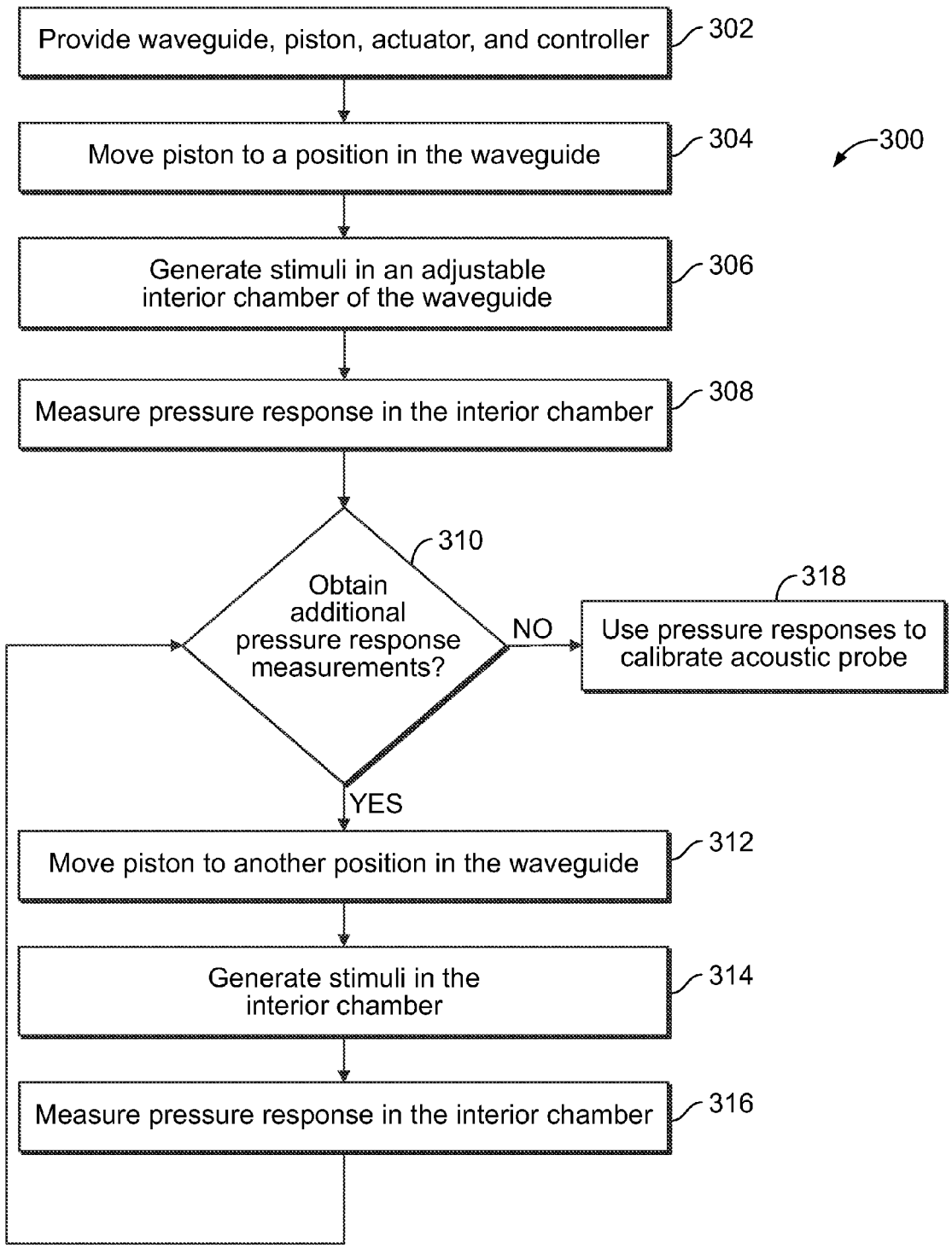
FIG. 3 illustrates a flowchart of a method for calibrating an acoustic probe.

FIG. 3 illustrates a flowchart of a method 300 for calibrating an acoustic probe. The method 300 may be used in conjunction with the system 100 shown in FIGS. 1 and 2. At 302, the waveguide 102, the piston 104, the actuator 128, and/or the controller device 130 described above are provided. During 302, the acoustic probe 112 is coupled with the waveguide 102 to form an enclosed (e.g., sealed) chamber (e.g., chamber 122) within the waveguide 102 between the acoustic probe 112 and the piston 104.

At 304, the piston 104 is moved to a position within the waveguide 102. At 306, a chirp stimuli is generated (e.g., by the sound source transducer 118 of the acoustic probe 112). At 308, the acoustic probe 112 measures data that is representative of a pressure response of the interior chamber 122 between the acoustic probe 112 and the piston 104 to the chirp stimuli (or other stimuli). For example, the microphone 120 of the acoustic probe 112 may be sensitive to an acoustic response of the acoustic stimuli that is representative of pressure in the interior chamber 122 of the waveguide 102 and/or may generate data that is representative of the pressure in the interior chamber 122.

At 310, a determination is made as to whether additional measurements are to be performed with a varying-size interior chamber 122. If one or more measurements are to be obtained, then flow of the method 300 can proceed to 312. If no more measurements are to be obtained, then flow of the method 300 can proceed to 318.

At 312, the piston 104 is moved to a different position within the waveguide 102 to change a size of the interior chamber 122 in the waveguide 102. At 314, the acoustic probe 112 generates chirp stimuli (or other stimuli), similar to as described above. At 316, the acoustic probe 112 measures data that is representative of the pressure response to the stimuli, as described above. Flow of the method 300 may then return to 310 determine if one or more additional pressure response measurements are to be obtained.

At 318, the measurements obtained within the varying-size interior chamber 122 of the same waveguide 102 are used to calibrate the acoustic probe 112, as described above.

The method 300 may proceed in a loop-wise manner to move the piston 104 to other locations such that additional measurements of the pressure responses may be obtained at different positions of the piston 104 and at corresponding different sizes of the interior chamber 122. The pressure responses and sizes of the interior chamber 122 (or length dimensions 124 between the acoustic probe 112 and the piston 104) can be used to calibrate the acoustic probe 112, such as by calibrating Thévenin source pressure and impedance of the acoustic probe 112.

In another embodiment, an acoustic probe calibration system includes a waveguide and a moveable piston. The waveguide extends from a front end to an opposite back end along a longitudinal axis. The waveguide defines a cavity extending from the front end to the back end. The moveable piston is disposed within the cavity of the waveguide and is configured to move within the cavity of the waveguide along the longitudinal axis of the waveguide. An acoustic probe is inserted into the waveguide to define an interior chamber between the acoustic probe and the piston. The acoustic probe measures data that is representative of pressure responses to acoustic stimuli inside the interior chamber. The piston is moveable to a plurality of different positions within the waveguide to change a size of the interior chamber such that the acoustic probe can measure the data that is representative of the pressure responses within the varying-size interior chamber.

In another aspect, the piston is moveable within the waveguide relative to the waveguide without removing the acoustic probe from the waveguide or moving the acoustic probe relative to the waveguide.

In another aspect, the system also includes an actuator that moves the piston along the longitudinal axis of the waveguide within the waveguide to change the size of the interior chamber.

In another aspect, the system also includes a controller device coupled with the actuator and configured to drive the actuator to move the piston within the waveguide.

In another aspect, the controller device is configured to move the piston to each of a plurality of different predetermined positions within the waveguide.

In another aspect, the piston is moveable within the waveguide such that the acoustic probe measures the data that is representative of the pressure responses at a plurality of different resonant frequencies of the acoustic stimuli within the same waveguide.

In another aspect, the piston is moveable within the waveguide such that the acoustic probe measures the data that is representative of the pressure responses to the acoustic stimuli within the varying-size interior chamber within the same waveguide.

In another aspect, the size of the interior chamber of the waveguide into which the acoustic stimuli are transmitted and in which the data that is representative of the pressure responses are measured is based on the position of the piston within the waveguide.

In another embodiment, a method for calibrating an acoustic probe includes positioning a piston at a first position within a waveguide that extends from a front end to an opposite back end along a longitudinal axis. The waveguide defines a cavity that extends from the front end to the back end. The method also includes inserting the acoustic probe within the waveguide. The acoustic probe and the piston define an interior chamber within the cavity of the waveguide that extends from the acoustic probe to the piston. The method also includes emitting acoustic stimuli into the interior chamber from the probe and measuring data that is representative of one or more first pressure responses to the acoustic stimuli. The method further includes moving the piston to a different, second position within the waveguide such that a size of the interior chamber in the waveguide changes, emitting acoustic stimuli into the interior chamber from the probe, and measuring data that is representative of one or more second pressure responses to the acoustic stimuli.

In another aspect, the method also includes calibrating the acoustic probe based on the data that is representative of at least the first and second pressure responses obtained from the varying-size interior chamber of the same waveguide.

In another aspect, moving the piston includes displacing the piston within the waveguide relative to the waveguide without removing the acoustic probe from the waveguide or moving the acoustic probe relative to the waveguide.

In another embodiment, an acoustic probe calibration system includes a piston, an actuator, and a controller device. The piston is configured to be positioned in a cavity of a waveguide that extends from a front end to an opposite back end along a longitudinal axis. The actuator is configured to be coupled with the piston and to move the piston within the cavity along the longitudinal axis of the waveguide. The controller device is configured to direct the actuator to move the piston between a series of different positions within the waveguide. The controller device is configured to the actuator to move the piston to the different positions in order to define a varying-size interior chamber between an acoustic probe coupled to the front end or the back end of the waveguide and the piston in the waveguide. The controller device is configured to move the piston to the different positions such that the acoustic probe measures data that is representative of pressure responses to acoustic stimuli inside the varying-size interior chamber at the different positions of the piston.

In another aspect, the controller device is configured to be manually controlled to move the piston to one or more of the different positions in the waveguide.

In another aspect, the controller device is configured to autonomously move the piston between the different positions.

In another aspect, the piston is moveable within the waveguide such that the acoustic probe measures the data that is representative of the pressure responses at a plurality of different resonant frequencies of the acoustic stimuli within the same waveguide.

In another aspect, the piston is moveable within the waveguide such that the acoustic probe measures the data that is representative of the pressure responses to the acoustic stimuli within a varying-size interior chamber within the same waveguide.

In another aspect, the varying-sizes interior chamber of the waveguide, into which the acoustic stimuli are transmitted by the acoustic probe and in which the data that is representative of the pressure responses is measured, is based on the position of the piston within the waveguide.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are example embodiments. Many other embodiments will be apparent to one of ordinary skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the inventive subject matter and to enable a person of ordinary skill in the art to practice the embodiments disclosed herein, including making and using any devices or systems and performing any incorporated methods. The patentable scope of the subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the disclosed subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods, without departing from the spirit and scope of the subject matter herein involved, it is intended that all of the subject matter of the above description or shown in the accompanying drawings shall be interpreted merely as examples illustrating the inventive concepts herein and shall not be construed as limiting the disclosed subject matter.

What is claimed is:

1. An acoustic probe calibration system comprising:
   a waveguide extending from a front end to an opposite back end along a longitudinal axis, the waveguide defining a cavity extending from the front end to the back end; and
   a moveable piston disposed within the cavity of the waveguide, the piston configured to move within the cavity of the waveguide along the longitudinal axis of the waveguide;
   wherein an acoustic probe is inserted into the waveguide to define an interior chamber between the acoustic probe and the piston, the acoustic probe configured to measure data that is representative of pressure responses to acoustic stimuli inside the interior chamber;
   wherein the piston is moveable to a plurality of different positions within the waveguide to change a size of the interior chamber such that the acoustic probe is configured to measure the data that is representative of the pressure responses to the acoustic stimuli within the varying-size interior chamber; and
   a processor programmed to calibrate the acoustic probe based on the data that is representative of the pressure responses to the acoustic stimuli within the varying-size interior chamber of the same waveguide.

2. The system of claim 1, wherein the piston is moveable within the waveguide relative to the waveguide without removing the acoustic probe from the waveguide or moving the acoustic probe relative to the waveguide.

3. The system of claim 1, further comprising an actuator that moves the piston along the longitudinal axis of the waveguide within the waveguide to change the size of the interior chamber.

4. The system of claim 3, further comprising a controller device coupled with the actuator, the controller device configured to drive the actuator to move the piston within the waveguide.

5. The system of claim 4, wherein the controller device is configured to move the piston to each of a plurality of different predetermined positions within the waveguide.

6. The system of claim 1, wherein the piston is moveable within the waveguide such that the acoustic probe measures the data that is representative of the pressure responses at a plurality of different resonant frequencies to the acoustic stimuli within the same waveguide.

7. The system of claim 1, wherein the piston is moveable within the waveguide such that the acoustic probe measures the data that is representative of the pressure responses to the acoustic stimuli within the varying-size interior chamber within the same waveguide.

8. The system of claim 1, wherein the size of the interior chamber of the waveguide, into which the acoustic stimuli are transmitted and in which the data that is representative of the pressure responses are measured, is based on the position of the piston within the waveguide.

9. A method for calibrating an acoustic probe, the method comprising:
   positioning a piston at a first position within a waveguide that extends from a front end to an opposite back end along a longitudinal axis, the waveguide defining a cavity that extends from the front end to the back end;
   inserting the acoustic probe within the waveguide, the acoustic probe and the piston defining an interior chamber within the cavity of the waveguide that extends from the acoustic probe to the piston;
   emitting acoustic stimuli into the interior chamber from the acoustic probe and measuring data that is representative of one or more first pressure responses to the acoustic stimuli;
   moving the piston to a different, second position within the waveguide such that a size of the interior chamber in the waveguide changes;
   emitting acoustic stimuli into the interior chamber from the acoustic probe and measuring data that is representative of one or more second pressure responses to the acoustic stimuli; and
   calibrating the acoustic probe based on the data that is representative of at least the first and second pressure responses to the acoustic stimuli obtained within the varying-size interior chamber of the same waveguide.

10. The method of claim 9, wherein moving the piston includes displacing the piston within the waveguide relative to the waveguide without removing the acoustic probe from the waveguide or moving the acoustic probe relative to the waveguide.

11. An acoustic probe calibration system comprising:
    a piston configured to be positioned in a cavity of a waveguide that extends from a front end to an opposite back end along a longitudinal axis;
    an actuator configured to be coupled with the piston and to move the piston within the cavity along the longitudinal axis of the waveguide;
    a controller device configured to direct the actuator to move the piston between a series of different positions within the waveguide, the controller device for directing the actuator to move the piston to the different positions in order to define a varying-size interior chamber between an acoustic probe coupled to the front end or the back end of the waveguide and the piston in the waveguide, wherein the controller device is configured to move the piston to the different positions such that the acoustic probe measures data that is representative of pressure responses to acoustic stimuli inside the varying-size interior chamber at the different positions of the piston; and a processor programmed to calibrate the acoustic probe based on the data that is representative of the pressure responses to the acoustic stimuli within the varying-size interior chamber of the same waveguide.

12. The system of claim 11, wherein the controller device is configured to be manually controlled to move the piston to one or more of the different positions in the waveguide.

13. The system of claim 11, wherein the controller device is configured to autonomously move the piston between the different positions.

14. The system of claim 11, wherein the piston is moveable within the waveguide such that the acoustic probe measures the data that is representative of the pressure responses at a plurality of different resonant frequencies to the acoustic stimuli within the same waveguide.

15. The system of claim 11, wherein the piston is moveable within the waveguide such that the acoustic probe measures the data that is representative of the pressure responses to the acoustic stimuli within the varying-size interior chamber within the same waveguide.

16. The system of claim 11, wherein a size of the varying-size interior chamber of the waveguide, into which the acoustic stimuli are transmitted by the acoustic probe and in which the data that is representative of the pressure responses is measured, is based on the position of the piston within the waveguide.

* * * * *